United States Patent
Proksa

(10) Patent No.: US 7,813,472 B2
(45) Date of Patent: Oct. 12, 2010

(54) CT IMAGING SYSTEM

(75) Inventor: Roland Proksa, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 12/517,254

(22) PCT Filed: Nov. 29, 2007

(86) PCT No.: PCT/IB2007/054834

§ 371 (c)(1),
(2), (4) Date: Jun. 2, 2009

(87) PCT Pub. No.: WO2008/068674

PCT Pub. Date: Jun. 12, 2008

(65) Prior Publication Data

US 2010/0061504 A1   Mar. 11, 2010

(30) Foreign Application Priority Data

Dec. 4, 2006   (EP)   ................. 06125341

(51) Int. Cl.
*A61B 6/00*   (2006.01)
(52) U.S. Cl. ................ 378/4; 378/19; 378/901
(58) Field of Classification Search ................ 378/4–20, 378/51–59, 62, 901; 382/130–132; 600/425, 600/431
See application file for complete search history.

(56) References Cited

U.S. PATENT DOCUMENTS

| 4,887,604 | A | 12/1989 | Shefer et al. |
| 6,373,920 | B1 | 4/2002 | Hsieh |
| 2004/0101090 | A1 | 5/2004 | Drummond et al. |
| 2004/0184574 | A1 | 9/2004 | Wu et al. |
| 2005/0058331 | A1 | 3/2005 | Klotz |
| 2009/0086882 | A1* | 4/2009 | Grasruck et al. ............... 378/4 |

FOREIGN PATENT DOCUMENTS

EP   0600673 A2   6/1994

OTHER PUBLICATIONS

Llopart, X., et al.; Medipix2: a 64-k Pixel Readout chip with 55-um Square Elements Working in Single Photon Counting Mode; 2002; IEEE Trans. on Nuclear Science; 49(5)2279-2283.
Llopart, X., et al.; First test measurements of a 64k pixel readout chip working in single photon counting mode; 2003; Nuclear Instruments and Methods in Physics Research; A509:157-163.
Cenic, A., et al.; Dynamic CT Measurements of Cerebral Blood Flow: A Validation Study; 1999; AJNR; 20:63-73.

* cited by examiner

*Primary Examiner*—Courtney Thomas

(57) ABSTRACT

The invention relates to a CT imaging system for determining the flow of a substance within an object, wherein the CT imaging system comprises a polychromatic X-ray source and an energy-resolving X-ray detector for obtaining detection signals depending on the X-ray radiation after passing through the object. A calculation unit (12) determines a k-edge 5 component of the substance from the detection signals, and a reconstruction unit (13) reconstructs a time series of k-edge image from the determined k-edge component. A flow determination unit (14) determines flow values indicative for the flow within the object from the time series of k-edge images.

20 Claims, 3 Drawing Sheets

CT IMAGING SYSTEM

FIELD OF THE INVENTION

The present invention relates to a CT imaging system, a CT method and a computer program for determining the flow of a substance within an object. The invention relates further to a corresponding determination device, determination method and computer program for determining the flow of a substance within an object.

BACKGROUND OF THE INVENTION

Conventional CT imaging systems for determining the flow of a substance within an object use an X-ray source which emits X-ray radiation and a detection unit detecting detection signals depending on the x-ray radiation after passing through the object. The detection signals are used by a reconstruction unit to reconstruct times series of images of the object, wherein flow values indicative for the flow of the substance within the object are determined from the time series of images of the object. These flow values are for example the substance flow or the mean transit time through the object.

By using these conventional CT imaging systems, the determination of the flow values is influenced by effects related to the passage of the X-ray radiation through the object, i.e. the X-ray radiation is not only influenced by the substance, for which the flow is to be determined, but also by the object itself. This diminishes the quality of the determined flow values.

SUMMARY OF THE INVENTION

It is therefore an object of the present invention to provide a CT imaging system wherein the influence of the determination of the flow values by effects related to the passage of the X-ray radiation through the object is reduced, thereby increasing the quality of the determined flow values. Further, a corresponding CT imaging method, a corresponding determination device and a corresponding determination method shall be provided.

In a first aspect of the present invention a CT imaging system for determining the flow of a substance within an object is presented that comprises
- a polychromatic X-ray source for emitting polychromatic X-ray radiation,
- an energy-resolving X-ray detector for obtaining detection signals depending on said X-ray radiation after passing through said object energy-resolved,
- a calculation unit for determining a k-edge component of the substance from the detection signals,
- a reconstruction unit for reconstructing a time series of k-edge images from the determined k-edge component,
- a flow determination unit for determining flow values indicative for the flow of the substance within the object from the time series of k-edge images.

The present invention is based on the idea that a k-edge component of the substance is determined from the detection signals and that a time series of k-edge images is reconstructed from the determined k-edge component. This leads to reconstructed images only containing the substance, i.e., the object itself is not contained in the image. These images of the substance are therefore not disturbed by the object. Since these images containing only the substance are used for determining the flow values, the influence of the flow values by effects related by to the passage of the X-ray radiation through the object is reduced, thereby increasing the quality of the determined flow values.

The flow determination unit is preferably adapted for determining a mean transit time of the substance through the object as a flow value. Furthermore, the flow determination unit can be adapted for determining the substance flow as a flow value. Since the mean transit time and the substance flow are determined from the time series of k-edge images containing only the substance, the mean transit time and the substance flow can be determined with a quality which is improved in comparison to respective values determined with conventional CT image systems.

In a preferred embodiment, a substance is present within a fluid within the object and the flow determination unit is adapted to calibrate the reconstructed time series of k-edge images with respect to the fluid and to determine flow values indicative for the flow of the fluid within the object from the calibrated reconstructed time series of k-edge images. Since the reconstructed time series of k-edge images are calibrated with respect to the fluid, flow values can be determined indicative for the flow of the fluid within the object. This allows to directly determine the flow values, in particular the mean transit time of the fluid through the object and the fluid flow, quantitatively. In contrast, a conventional CT perfusion system allows only an indirect quantification of the flow based on a shift in the x-ray attenuation.

The fluid can be blood of a human or animal body. This allows to determine for example the mean transit time and/or the flow of the blood within a human or animal body, in particular within the brain. Therefore, for example, the cerebral blood flow (CBF) can be determined.

It is preferred that the energy-resolving X-ray detector is adapted for providing a plurality of energy-resolved detection signals for a plurality of energy bins wherein the calculation unit is adapted for determining the k-edge component of the substance by solving a system of equations for the plurality of energy-resolved detection signals, using a model for the detection signals describing a detection signal as a combination of the k-edge effect of the substance, the photo-electric effect and the compton effect, each effect contributing with a corresponding component to the detection signal. In particular, the X-ray detector provides a number of energy resolved detection signals with different energy bins, different energy bins comprising different spectral sensitivities, in particular each energy bin being a section of the complete energy range in which the detection signal is available and of interest. The scanned object is than modeled as a combination of the photo-electric effect with a first spectrum, the Compton effect with a second spectrum and the substance with a k-edge in the interesting energy range with a third spectrum. The density length product for each of the components in each detection signal is modeled as a discrete linear system which is solved to obtain at least the k-edge components of the substance. From the k-edge components of the substance obtained for different detector positions a k-edge image of the substance can than be reconstructed with a conventional reconstruction method.

The system of equations for the plurality of energy resolved detection signals is preferably solved by use of a numerical method. A preferred method is a maximum likelihood approach that takes noise statistics of the measurement into account.

In a further preferred embodiment a model is used which takes account of the emission spectrum of the X-ray source and the spectral sensitivity of the X-ray detector in each of the plurality of energy bins. That leads to higher accuracy of the calculated components and, thus, of the reconstructed images and of the determined flow values.

The substance is preferentially a contrast agent injected into the object, in particular into a human or animal body. This allows to determine flow values of a human or animal body, for example, the mean transit time of blood through an organ of a human body or the blood flow.

A corresponding CT imaging method and a corresponding computer program are defined herein. A corresponding determination device, a corresponding determination method and a corresponding computer program for determining the flow of a substance within an object are defined herein. Preferred embodiments of the invention are defined in the independent claims.

BRIEF DESCRIPTION OF THE DRAWINGS

These and other aspects of the invention will be apparent from and elucidated with reference to the embodiments described hereinafter.

DETAILED DESCRIPTION OF EMBODIMENTS

Figure 1:
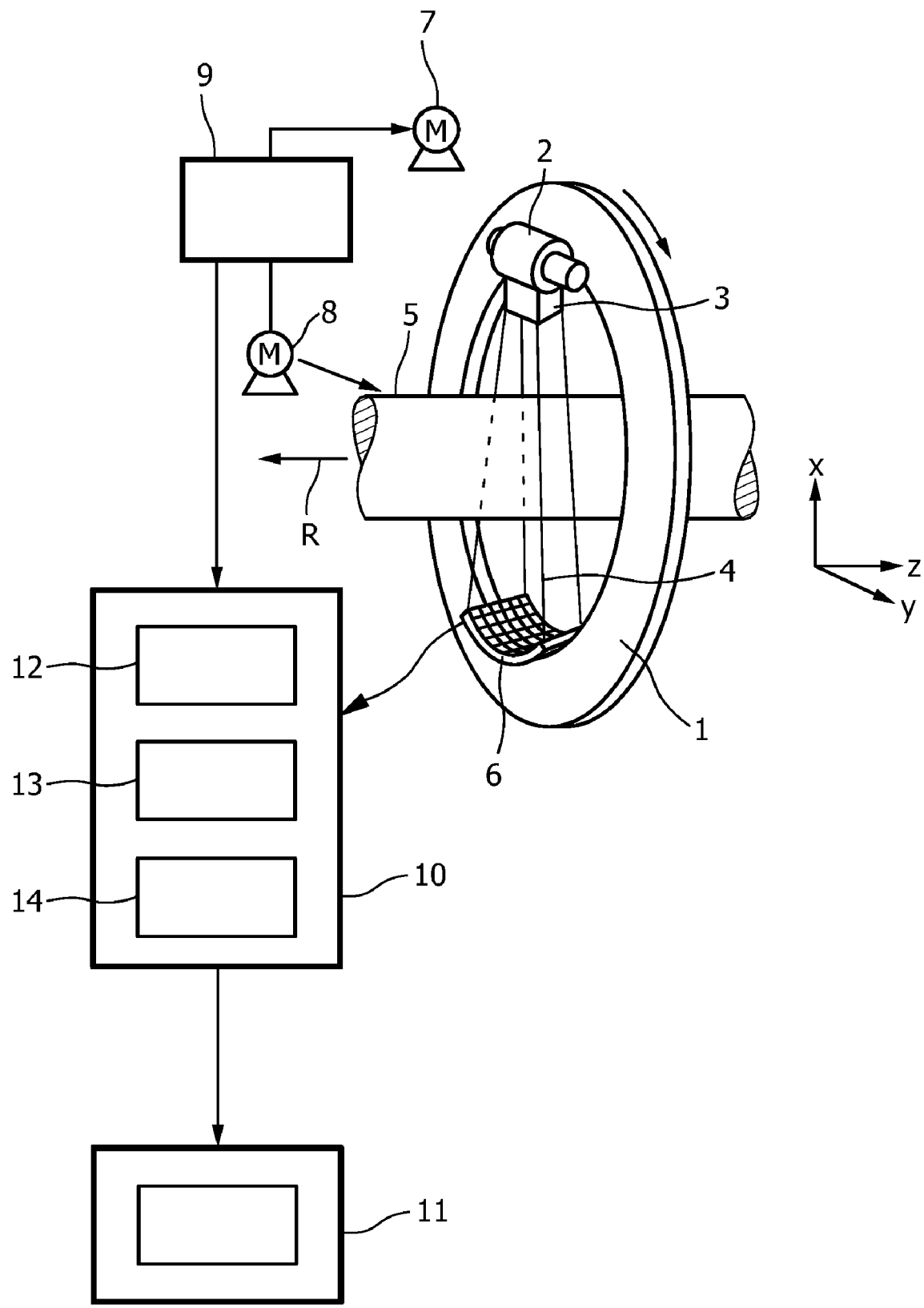
FIG. 1 shows a diagrammatic representation of a CT imaging system in accordance with the invention.

The CT imaging system shown in FIG. 1 includes a gantry 1 which is capable of rotating about an axis of rotation R which extends parallel to the z direction. A radiation source 2, for example an X-ray tube, is mounted on the gantry 1. The X-ray source is provided with a collimator device 3 which forms a conical radiation beam 4 from the radiation emitted by the X-ray source 2. In other embodiments, the collimator device 3 can be adapted for forming a radiation beam having another shape, for example, having a fan shape.

The radiation traverses an object (not shown), such as a patient, in a region of interest in a cylindrical examination zone 5. After having traversed the examination zone 5, the X-ray beam 4 is incident on an energy-resolving X-ray detector unit 6, in this embodiment a two-dimensional detector, which is mounted on the gantry 1. In another embodiment, the energy-resolving X-ray detector unit can be a one-dimensional detector.

Energy-resolving X-ray detectors work, for example, on the principle of counting the incident photons and output a signal that shows the number of photons per energy in a certain energy area. Such an energy-resolving detector is, for instance, described in Llopart, X., et al. "First test measurements of a 64 k pixel readout chip working in a single photon counting mode", Nucl. Inst. and Meth. A, 509 (1-3): 157-163, 2003 and in Llopart, X., et al., "Medipix2: A 64-k pixel readout chip with 55 mum square elements working in a single photon counting mode", IEEE Trans. Nucl. Sci. 49(5): 2279-2283, 2002.

The gantry 1 is driven at a preferably constant but adjustable angular speed by a motor 7. A further motor 8 is provided for displacing the object, for example, the patient who is arranged on a patient table in the examination zone 5, parallel to the direction of the axis of rotation R or the z axis. These motors 7, 8 are controlled by a control unit 9, for instance, such that the radiation source 2 and the examination zone 5 move relative to one another along a helical trajectory. But is preferred, that the object or the examination zone 5 is not moved and that the X-ray source 2 is rotated, i.e. that the X-ray source 2 travels along a circular trajectory relative to the object.

The data acquired by the detector 6 are provided to an determination device 10 for determining the flow of a substance within an object, in particular for determining flow values indicative for the flow within the object. These flow values can for example be the mean transit time or the substance flow through the object. If the object is for example a human brain, the determination device can be adapted to determine the cerebral blood flow and the cerebral mean transit time. The flow values can finally be provided to a display unit 11 for displaying the flow values. The display unit 11 can display single flow values or average flow values which correspond to a certain region within the object, it is preferred that the display unit 11 shows a two-dimensional or three-dimensional image, wherein each image element, i.e. each pixel or each voxel, respectively, shows the flow values at the location within the object which corresponds to the respective image element. Thus, the display unit 11 shows preferably an image of flow values.

The determination device 10 comprises a calculation unit 12 for determining a k-edge component from the detection signals acquired by the detector 6. The determination device 10 further comprises a reconstruction unit 13 for reconstructing a time series of k-edge images from the determined k-edge component, and the determination device 10 comprises a flow determination unit 14 for determining flow values indicative for the flow within the object from the time series of k-edge images. Also the determination device 10 is preferentially controlled by the control unit 9.

Figure 2:
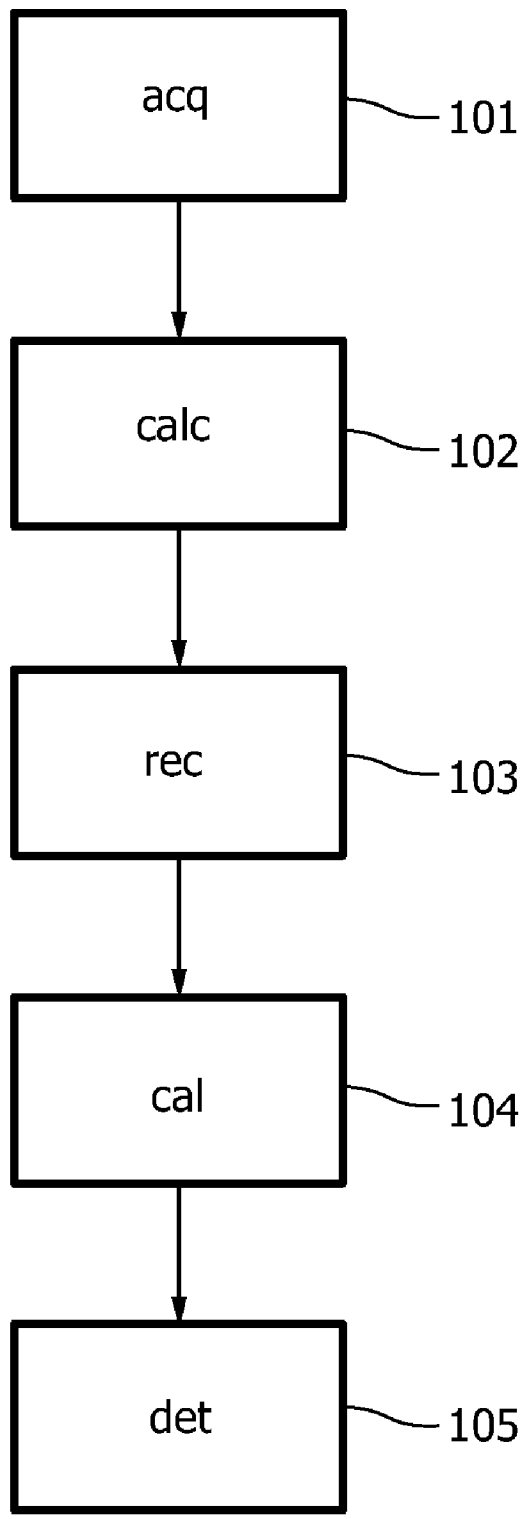
FIG. 2 shows a flow chart illustrating an embodiment of a CT imaging method for determining the flow of a substance within an object.

In the following an embodiment of an CT imaging method for determining the flow within an object in accordance with the invention will be described in more detail with respect to the flow chart shown in FIG. 2.

In step 101 the X-ray source 2 rotates around the axis of rotation R or the z direction, and the object is not moved, i.e. the X-ray source 2 travels along a circular trajectory around the object. In another embodiment, the X-ray source 2 can move along another trajectory, for example a helical trajectory, relative to the object. The X-ray source 2 emits X-ray radiation traversing the object in which a substance is present. The substance is for example a contrast agent, based on iodine or gadolinium, which has been injected prior to this step 101. The object is for example a human or animal body, wherein the contrast agent has been injected into, for example, blood vessels of the human or animal body. The X-ray radiation, which has passed the object and the substance within the object, is detected by the detector 6, which generates detection signals. Thus, in step 101 detection signals are acquired.

In step 102 the detection signals are transmitted to the calculation unit 12 of the determination device 10. The calculation unit 12 determines a k-edge component of the substance from the detection signals. This will now be explained in more detail.

Figure 3:
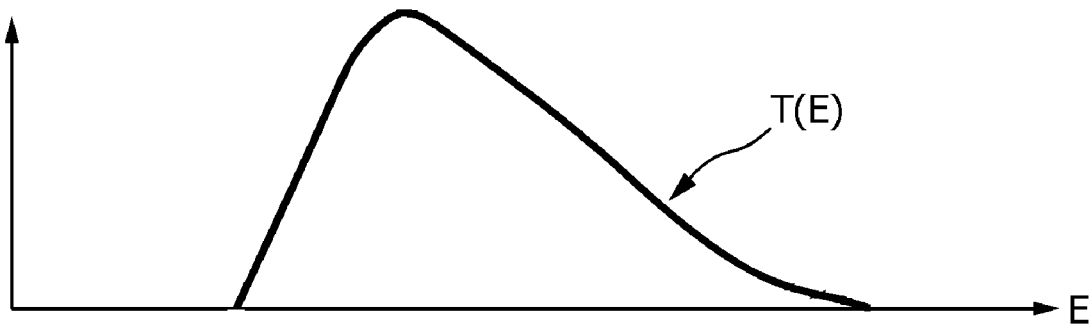
FIG. 3 shows exemplary a spectrum of a polychromatic X-ray source.

The input to the calculation unit 12 are energy-resolved detections signals $d_i$ for a plurality, at minimum three, energy bins. These detection signals $d_i$ show a spectral sensitivity $D_i(E)$ of the i-th energy bin $b_i$. Furthermore, the emission spectrum $T(E)$ of the polychromatic X-ray tube 2 is generally known, or can be measured prior to step 101. An example for such an emission spectrum $T(E)$ of a polychromatic X-ray tube is schematically shown in FIG. 3. In the determination device, in particular, in the calculation unit 12, the generation of the detection signals $d_i$ is modeled as a linear combination of the photo-electric effect with spectrum P(E), the Compton effect with spectrum C(E) and the substance with a k-edge in the interesting energy range and spectrum K(E).

Figure 4:
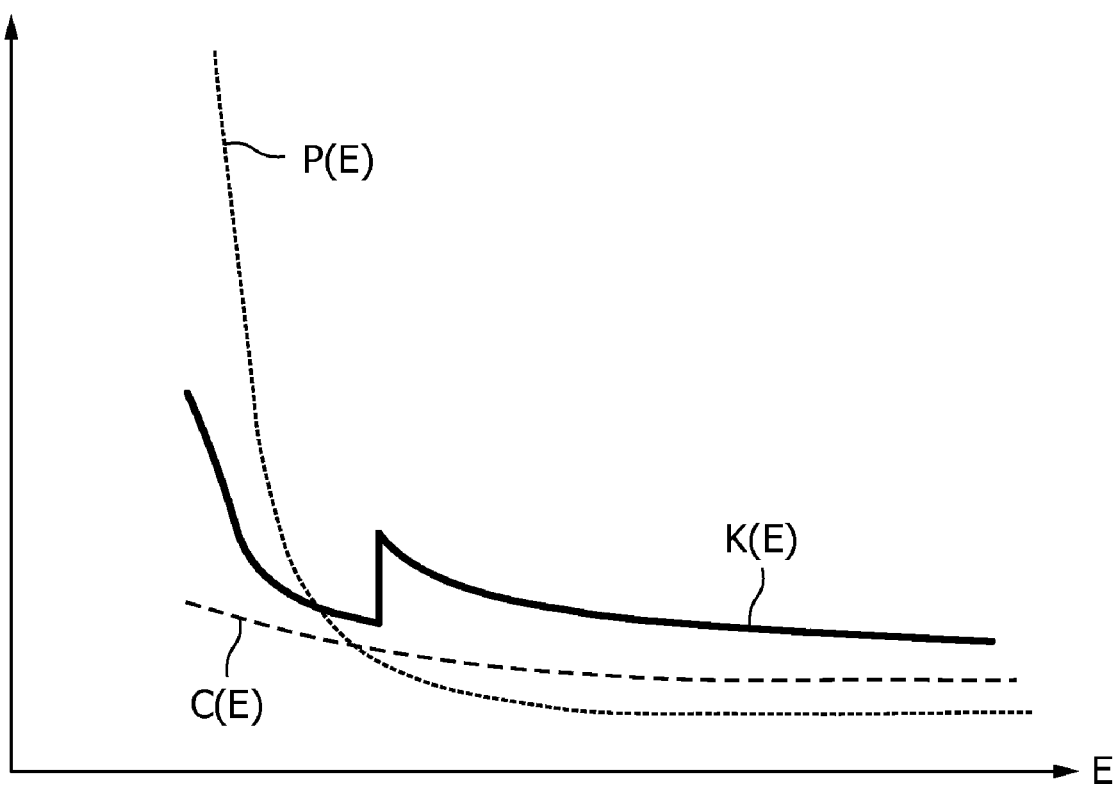
FIG. 4 shows exemplary spectra of a photo-electric effect, a contempt effect and of a substance within an object.

Spectra P(E), C(E) and K(E) are exemplarily shown in FIG. 4.

The generation of the detection signals can be modeled by following linear system:

$$d_i = \int dE\, T(E) D_i(E) \exp[-(\rho_{photo} P(E) + \rho_{compton} C(E) + \rho_{k\text{-}edge} K(E,))]. \quad (1)$$

wherein $\rho_{photo}$, $\rho_{compton}$, $\rho_{k\text{-}edge}$ are the density length products of the photo-electric component, the Compton component and the k-edge component, respectively.

Since at least three detection signals $d_1, d_2, d_3$ are available for the at least three energy bins $b_1, b_2, b_3$, a system of at least three equations is formed having three unknowns, which are the three density length products, which can thus be solved with known numerical methods in the calculation unit 12. If more than three energy bins are available, it is preferred to use a maximum likelihood approach that takes the noise statistics of the measurements into account. Generally, three energy bins are sufficient. In order to increase the sensitivity and noise robustness, however, it is preferred to have more detection signals for more energy bins.

In step 103 the determined k-edge component, i.e. the density length product $\rho_{k\text{-}edge}$, is transmitted to the reconstruction unit 13. Since the X-ray source 2 moves relative to the object, the detection signals, and therefore, the determined density products $\rho_{k\text{-}edge}$, correspond to X-rays having traversed the object and the substance in different angular directions. Thus, a k-edge image can be reconstructed by using conventional CT reconstruction methods, like a filtered backprojection of the density length product $\rho_{k\text{-}edge}$. The acquisition step 101 is performed such that a time series of k-edge images of the same location within the object can be reconstructed. This means, for example, that the X-ray tube 2 travels along a circular trajectory around the object and acquires detection signals over a time period being long enough in order to acquire detections signals with which at least for a field of interest a group of images can be reconstructed, wherein the images of the group show the same location within the object, but at different time points. Such a group is a time series of k-edge images of an object, in particular, of an field of view of an object, i.e. a four-dimensional image data set.

In step 104 the k-edge images are calibrated with respect to the substance within the object. In particular, the substance is present within a fluid within the object, and the k-edge images are calibrated with respect to the fluid within the object. It is preferred, that the object is a human or animal body, or a part of a body, like the brain, and that the fluid is blood. The calibration can be performed by selecting an image region comprising one or more image elements, i.e. pixels or voxels, which correspond to the fluid only. Since the volume of the respective region of the object is known, also the volume of the fluid within this region is known. Furthermore, the values of the image elements within this region of the object relate to the amount of the substance within this region. Therefore, a direct relation between the fluid volume and the amount of the substance shown in the k-edge image can be determined. This relation can be used to calibrate the k-edge images such that they show the fluid volume in each image element, i.e. in each pixel or voxel. This calibration can be performed by the reconstruction unit 13 or the flow determination unit 14. As a simple example, if the reconstructed substance concentration in an image element is $c_s$ and if the fluid volume in this image element is V, each value of the reconstructed four-dimensional image data set can be multiplied by $V/c_s$, in order to calibrate the four-dimensional image data set, i.e. the time series of k-edges images.

In step 105 the flow determination unit 14 receives the calibrated time series of images and determines flow values indicative for the flow within the object from the received time series of images. Since the calibrated images show directly the blood value at different locations within the object and at different time points, these calibrated images show directly the flow of the substance.

The determination of flow values from the calibrated images, i.e. from the determined flow of the substance, is well known. These flow values are, for example, the mean transit time, the cerebral blood flow or the cerebral blood volume. A determination of flow values is, for example, described in "Dynamic CT Measurement of Cerebral Blood Flow: A Validation Study", Aleksa Cenic, Darius G. Nabavi, Rosemary A. Craen, Adrian W. Gelb and Ting-Yim Lee, American Journal of Neuroradiology 20:63-73 (1999).

While the invention has been illustrated and described in detail in the drawings and forgoing description, such illustration and description are to be considered illustrative or exemplary and not restrictive. The invention is not limited to the disclosed embodiment.

The object can be a whole object or only a part of an object. This part of an object can be a field of interest, which is predetermined, for example, by a user.

The object can be any object, in particular, the object can also be a technical object. Furthermore, the fluid can be any fluid within the object. In particular, the CT imaging system can also be adapted to determine flow values relating to a flow, for example of water or oil, within a technical object.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. The mere fact that certain features are recited in mutually different dependent claims does not indicate that a combination of these features cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. CT imaging system for determining the flow of a substance within an object, comprising:
   a polychromatic X-ray source for emitting polychromatic X-ray radiation,
   an energy-resolving X-ray detector for obtaining detection signals depending on the X-ray radiation after passing through the object,
   a calculation unit for determining a k-edge component of the substance from the detection signals,
   a reconstruction unit for reconstructing a time series of k-edge images from the determined k-edge component,
   a flow determination unit for determining flow values indicative of the flow within the object from the time series of k-edge images.

2. CT imaging system as claimed in claim 1, wherein the flow determination unit is adapted for determining a mean transit time of the substance through the object as a flow value.

3. CT imaging system as claimed in claim 1, wherein the flow determination unit is adapted for determining the substance flow as a flow value.

4. CT imaging system as claimed in claim 1, wherein the substance is present within a fluid within the object and wherein the flow determination unit or the reconstruction unit is adapted to calibrate the reconstructed time series of k-edge images with respect to the fluid and to determine flow values indicative for the flow of the fluid within the object from the calibrated reconstructed time series of k-edge images.

5. CT imaging system as claimed in claim 4, wherein the flow determination unit is adapted for determining the mean transit time of the fluid through the object as a flow value.

6. CT imaging system as claimed in claim 4, wherein the flow determination unit is adapted for determining the fluid flow as a flow value.

7. CT imaging system as claimed in claim 1, wherein the energy-resolving X-ray detector is adapted for providing a plurality of energy-resolved detection signals for a plurality of energy bins, and wherein the calculation unit is adapted for determining the k-edge component of the substance by solving a system of equations for the plurality of energy-resolved detection signals, using a model for the detection signals describing a detection signal as a combination of a k-edge effect of the substance, a photo-electric effect and a Compton effect, each effect contributing with a corresponding component to the detection signal.

8. CT imaging system as claimed in claim 7, wherein the calculation unit is adapted to use a model which takes account of the emission spectrum P(E) of the X-ray source and the spectral sensitivity of the X-ray detector in each of the plurality of energy bins.

9. Determination device for determining the flow of a substance within an object, the determination device being provided with detection signals, the detection signals being obtained by an energy resolving X-ray detector for obtaining detection signals depending on X-ray radiation emitted by a polychromatic X-ray after passing through the object, comprising:
a calculation unit for determining a k-edge component of the substance from the detection signals,
a reconstruction unit for reconstructing a time series of k-edge images from the determined k-edge component,
a flow determination unit for determining flow values indicative for the flow within the object from the time series of k-edge images.

10. The device of claim 9, wherein the energy-resolving X-ray detector is adapted for providing a plurality of energy-resolved detection signals for a plurality of energy bins, and wherein the calculation unit is adapted for determining the k-edge component of the substance by solving a system of equations for the plurality of energy-resolved detection signals, using a model for the detection signals describing a detection signal as a combination of a k-edge effect of the substance, a photo-electric effect and a Compton effect, each effect contributing with a corresponding component to the detection signal.

11. CT imaging method for determining the flow of a substance within an object, comprising the steps of:
emitting polychromatic X-ray radiation by a polychromatic X-ray source for,
obtaining detection signals depending on the X-ray radiation after passing through the object by an energy-resolving X-ray detector,
determining a k-edge component of the substance from the detection signals by a calculation unit,
reconstructing a time series of k-edge images from the determined k-edge component by a reconstruction unit,
determining flow values indicative for the flow within the object from the time series of k-edge images by a flow determination unit.

12. The method of claim 11, further comprising: determining a mean transit time of the substance through the object as the flow value.

13. The method of claim 11, wherein the substance is present within a fluid within the object, and further comprising:
calibrating the reconstructed time series of k-edge images with respect to the fluid; and
determining flow values indicative for the flow of the fluid within the object from the calibrated reconstructed time series of k-edge images.

14. The method of claim 11, further comprising:
providing a plurality of energy-resolved detection signals for a plurality of energy bins;
determining the k-edge component of the substance by solving a system of equations for the plurality of energy-resolved detection signals;
using a model for the detection signals describing a detection signal as a combination of a k-edge effect of the substance, a photo-electric effect and a Compton effect, each effect contributing with a corresponding component to the detection signal.

15. The method 14, further comprising:
using a model which takes account of an emission spectrum P(E) of the X-ray source and a spectral sensitivity of the X-ray detector in each of the plurality of energy bins.

16. Determination method for determining the flow of a substance within an object, the determination method being provided with detection signals, the detection signals being obtained by an energy resolving X-ray detector for obtaining detection signals depending on X-ray radiation emitted by a polychromatic X-ray after passing through the object, comprising:
determining a k-edge component of the substance from the detection signals by a calculation unit,
reconstructing a time series of k-edge images from the determined k-edge component by a reconstruction unit,
determining flow values indicative for the flow within the object from the time series of k-edge images by a flow determination unit.

17. The method of claim 16, further comprising: determining a mean transit time of the substance through the object as the flow value.

18. The method of claim 16, wherein the substance is present within a fluid within the object, and further comprising:
calibrating the reconstructed time series of k-edge images with respect to the fluid; and
determining flow values indicative for the flow of the fluid within the object from the calibrated reconstructed time series of k-edge images.

19. The method of claim 16, further comprising:
providing a plurality of energy-resolved detection signals for a plurality of energy bins;

determining the k-edge component of the substance by solving a system of equations for the plurality of energy-resolved detection signals;

using a model for the detection signals describing a detection signal as a combination of a k-edge effect of the substance, a photo-electric effect and a Compton effect, each effect contributing with a corresponding component to the detection signal.

20. The method 19, further comprising:

using a model which takes account of an emission spectrum $P(E)$ of the X-ray source and a spectral sensitivity of the X-ray detector in each of the plurality of energy bins.

* * * * *